United States Patent

Lavielle et al.

Patent Number: 5,250,544
Date of Patent: Oct. 5, 1993

[54] NEW PIPERIDINE TETRAHYDROPYRIDINE AND PYRROLIDINE COMPOUNDS

[75] Inventors: Gilbert Lavielle, La Celle Saint Cloud; Michel Laubie, Vaucresson; Francis Colpaert, Le Vesinet, all of France

[73] Assignee: Adir et Compagnie, Courbevoie, France

[21] Appl. No.: 723,757

[22] Filed: Jul. 1, 1991

[30] Foreign Application Priority Data

Jul. 10, 1990 [FR] France ............... 90 08729

[51] Int. Cl.$^5$ ............... A61K 31/445; C07D 211/06
[52] U.S. Cl. ............... 514/319; 514/321; 514/323; 546/197; 546/200; 546/205; 546/206
[58] Field of Search ............... 546/197, 200, 205, 206; 514/321, 323, 319

[56] References Cited

U.S. PATENT DOCUMENTS 3,847,613 11/1974 Sakazume ............... 546/172
4,443,462 4/1984 Carr ............... 546/206
4,757,079 7/1988 Gray ............... 546/206

OTHER PUBLICATIONS

Wouters, et al., European Journal of Pharmacology, 149 (1988) 213-223.

Primary Examiner—C. Warren Ivy
Assistant Examiner—Celia Chang
Attorney, Agent, or Firm—Gordon W. Hueschen

[57] ABSTRACT

The invention relates to compounds of formula I:

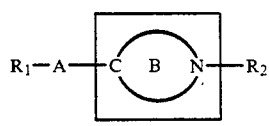

in which $R_1$ represents a naphthyl radical, a dihydronaphthyl radical, a tetrahydronaphthyl radical, a quinolyl radical or a 1,4-benzodioxanyl radical, A represents a single bond, a double bond, a methylene radical, a radical of formula $z_1$:

$$-CH= \quad (z_1)$$

or a radical of formula $z_2$:

$$=CH- \quad (z_2)$$

the ring B represents a piperidyl radical, a pyrrolidinyl radical, or a 1,2,3,6-tetrahydropyridyl radical, and $R_2$ represents: a hydrogen atom, a benzyl radical, or an alkyl radical having 1 to 6 carbon atoms, on condition that in one of these cases $R_1$ is other than a naphthyl ($y_1$), dihydronaphthyl ($y_2$) or tetrahydronaphthyl ($y_3$) radical and B is other than a piperidinyl radical, or an aminoalkyl radical having 1 to 6 carbon atoms, a cyanoalkyl radical having 1 to 6 carbon atoms, or a radical of formula $w_1$:

(List continued on next page.)

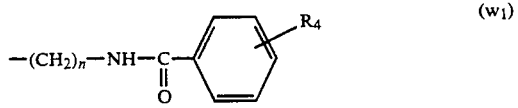

in which n is 1-6 and $R_4$ represents a hydrogen atom, a halogen atom, an alkyl radical having 1 to 6 carbon atoms, or an alkoxy radical having 1 to 6 carbon atoms, and their addition salts with a pharmaceutically-acceptable inorganic or organic acid, and medicaments containing the same.

6 Claims, 1 Drawing Sheet

U.S. PATENT DOCUMENTS

"Flesinoxan lowers blood pressure and heart rate in cats via 5-$HT_{1A}$ receptors".

Laubie, et al., European Journal of Pharmacology, 160 (1989) 385–394 "Ventrolated medullary pressor area: site of hypotensive and sympatho-inhibitory effects of (±)8-OH-DPAT in anaesthetized dogs".

Grohs, et al., Naunyn–Schmiedeberg's Arch Pharmacol (1990) 341, 472–475, "Cardiovascular effects of flesinoxan in anaesthetized and concious dogs".

Dabire, et al., European Journal of Pharmacology, 140 (1987) 259–266, "Comparison of effects of some 5-$HT_1$ agonists on blood pressure and heart rate of normotensive anaesthetized rats".

Ramage, et al., European Journal of Pharmacology, 151 (1988) 373–379, "Evidence that the novel antihypertensive agent, flesinoxan, causes differential sympathoinhibition and also increases vagal tone by a central action".

Hattersley et al "Some alkylation ....." J. Chem. Soc. (C) p. 217–22 (1969).

Webster Dictionary pp. 86 and 111.

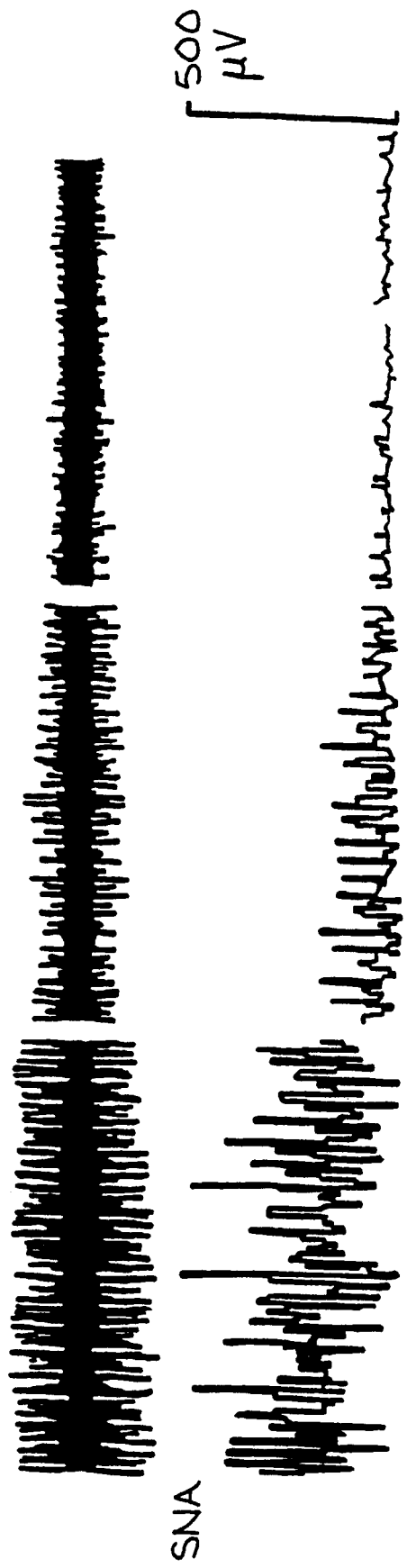

NEW PIPERIDINE TETRAHYDROPYRIDINE AND PYRROLIDINE COMPOUNDS

The present invention relates to new piperidine, tetrahydropyridine and pyrrolidine compounds.

Some 4-naphth-1-yl-1,2,3,6-tetrahydropyridine compounds having antiviral properties are described in the literature (EP 156,433).

4-(3,4-Dihydro-2-phenyl-1-napth-1-yl)piperidine compounds having contraceptive or sedative properties are also known (J. Med. Chem. (1967), 10(1), pp 78-84 Arzneim. Forsch., (1970), 20(9), pp 1235-1238 ; Int. J. Neuropharmacol. (1969), 8(2) pp 153-160) Acta. Pol. Pharm. (1967), Vol 24(5), pp 489-96 ; J.Chem. Soc. C. (1969) 2 pp 217-22).

Trifluoromethylphenyltetrahydropyridines are also used for the preparation of medicaments intended to control anxiety-depression disorders.

The compounds of the invention are distinguished from other piperidine, tetrahydropyridine and pyrrolidine compounds described in the literature and mentioned above by their original structures and by their pharmacological properties.

On the cardiovascular level, the compounds of the invention reduce the arterial pressure and the heart rate. This action results from a central inhibition of the sympathetic tonus and is associated with their $5\text{-}HT_{1A}$ agonist properties.

At the level of the central nervous system, the compounds Of the invention have demonstrated $5\text{-}HT_{1A}$ agonist properties.

They may therefore be useful in the treatment of hypertension, migraine, depression, anxiety, schizophrenia, stress and pain.

DESCRIPTION OF THE DRAWINGS

In the drawings, FIG. 1 is a graph and an amplified graph showing sympathetic nervous activity (SNA) as demonstrated for compounds of the invention according to Example 34.

The present invention relates more particularly to the compounds of general formula I:

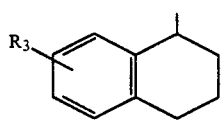

(I)

in which
$R_1$ represents a naphthyl radical, of formula $y_1$: a dihydronaphthyl radical, of formula $y_2$:

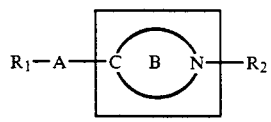

(y1)

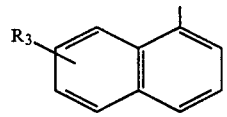

(y2)

a tetrahydronaphthyl radical of formula $y_3$:

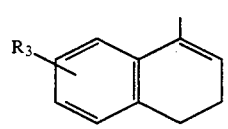

(y3)

in which formulae $R_3$ represents a hydrogen atom, a halogen atom, an alkyl radical having 1 to 6 carbon atoms, a hydroxyl radical or an alkoxy radical having 1 to 6 carbon atoms), a quinol-3-yl radical (optionally substituted on the benzene ring by one or more halogen atoms, alkyl radicals having 1 to 6 carbon atoms, hydroxyl radicals or alkoxy radicals having 1 to 6 carbon atoms) or a 1,4-benzodioxan-5-yl radical, A represents a single bond, a double bond (on condition, however, that $R_1$ represents a tetrahydronaphthyl radical), a methylene radical, a radical of formula $z_1$:

$$-CH= \quad (z_1)$$

or a radical of formula $z_2$: (on condition, however, that in this case $R_1$ represents a tetrahydronaphthyl radical), $$=CH- \quad (z_2)$$

the ring B represents a piperidyl radical (on condition, however, that in this case A represents a single or a double bond), a pyrrolidinyl radical (on condition, however, that in this case A represents a methylene radical, a radical $z_1$ or a radical $z_2$) or a 1,2,3,6-tetrahydropyridyl radical (on condition, however, that in this case A represents a single bond), and $R_2$ represents:
a hydrogen atom, a benzyl radical or an alkyl radical having 1 to 6 carbon atoms, on condition that in one of these cases $R_1$ is other than a naphthyl ($y_1$), dihydronaphthyl ($y_2$) or tetrahydronaphthyl ($y_3$) radical and B is other than a piperidinyl radical, or an aminoalkyl radical having 1 to 6 carbon atoms, a cyanoalkyl radical having 1 to 6 carbon atoms or a radical of formula $w_1$:

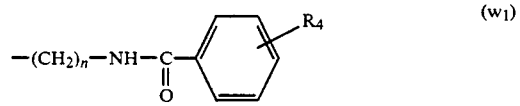

(w1)

(in which:
n is 1-6 and
$R_4$ represents a hydrogen atom, a halogen atom, an alkyl radical having 1 to 6 carbon atoms or an alkoxy radical having 1 to 6 carbon atoms), on condition, however, that
when $R_1$ is a radical $y_2$, $R_3$ represents a hydrogen atom, A a single bond and B a piperidyl radical, $R_2$ does not at the same time represent a methyl radical, and when $R_2$ is a radical $y_1$, $R_3$ represents a hydrogen atom, A a single bond and B a 1,2,3,6-tetrahydropyridyl radical, $R_2$ does not at the same time represent a hydrogen atom, and when $R_1$ is a radical $y_3$, $R_3$ represents a hydrogen atom, A a double bond and B a piperidyl radical, $R_2$ does not at the same time represent a methyl radical, its possible stereoisomers, and its addition salts with a pharmaceutically acceptable inorganic or organic acid.

The present invention also relates to a process for preparing compounds of general formula I, wherein: either a compound of formula II:

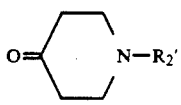
(II)

in which $R_{2'}$ represents an alkyl radical having 1 to 6 carbon atoms or a benzyl radical, is reacted with a compound of formula III:

$R_1-X$      (III)

in which $R_1$ has the same meaning as for the formula I and X represents a bromine or lithium atom or an MgBr group, to form the compounds of formula IV:

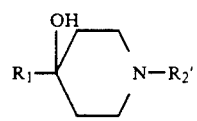
(IV)

in which $R_1$ has the meaning indicated above and $R_{2'}$ represents an alkyl radical having 1 to 6 carbon atoms or a benzyl radical, which is subjected to the action of hydrobromic acid to form the compounds of formula $I_a$:

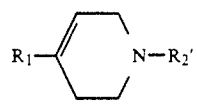
($I_a$)

in which $R_1$ has the same meaning as for the formula I and $R_{2'}$ represents an alkyl radical having 1 to 6 carbon atoms or a benzyl radical, and then either the compounds of formula $I_a$ are subjected to the action of ethyl chloroformate in the presence of an alkali metal inorganic salt to form the compounds of formula V:

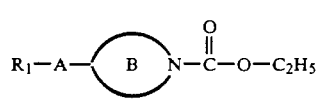
(V)

in which $R_1$ has the same meaning as for the formula I, A is a single bond and B represents a 1,2,3,6-tetrahydropyridyl radical, or the compounds of formula Ia are first subjected to a catalytic hydrogenation to form the compounds of formula $I_b$:

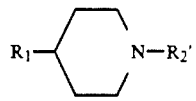
($I_b$)

in which $R_1$ has the same meaning as for the formula I and $R_{2'}$ represents an alkyl radical having 1 to 6 carbon atoms or a benzyl radical, then to the action of ethyl chloroformate in the presence of an alkali metal inorganic salt to form the compounds of formula V, in which $R_1$ has the same meaning as for the formula I and B represents a piperidyl radical, or a compound of formula VI:

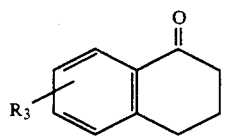
(VI)

in which $R_3$ has the same meaning as for the formula I, is reacted either with a compound of formula VII,

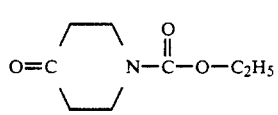
(VII)

to form the compounds of formula V in which $R_1$ represents a tetrahydronaphthyl radical of formula $y_3$, A is a double bond and B represents a piperidyl radical, or with a compound of formula VIII:

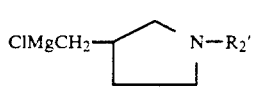
(VIII)

in which $R_{2'}$ has the same meaning as for the formula II, to form the compounds of formula IX:

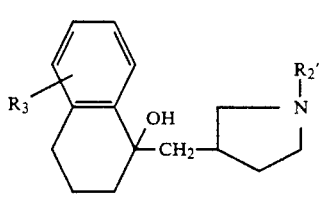
(IX)

in which the meaning of $R_3$ and $R_{2'}$ remains identical to that given above, which are subjected to the action of paratoluenesulfonic acid to form the compounds of formulae $I_c$ and $I_d$:

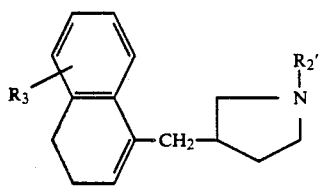
(Ic)

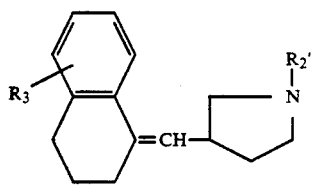
(Id)

in which formulae $R_3$ has the same meaning as for the formula I and the meaning of $R_{2'}$ is identical to that given for the formula II, which compounds are then separated then subjected to the action of ethyl chloroformate in the presence of an alkali metal inorganic salt to form the compounds of formula V, in which $R_1$ represents a dihydronaphthyl radical of formula $y_2$ or a tetrahydronaphthyl radical of formula $y_3$, A is, respectively, a methylene radical or a radical of formula $z_2$ and B represents a pyrrolidinyl radical, or with a compound of formula X:

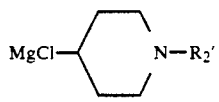
(X)

in which $R_{2'}$ has the same meaning as for the formula II, to form the compounds of formula XI:

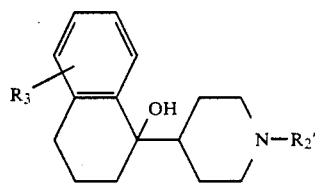
(XI)

in which the meaning of $R_3$ remains identical to that given for the formula I and $R_{2'}$ represents a benzyl radical or an alkyl radical having 1 to 6 carbon atoms, which compounds are then subjected to the action of para-toluenesulfonic acid to form the compounds of formula $I_e$:

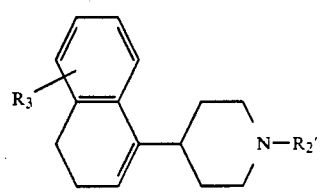
(Ie)

in which $R_3$ has the same meaning as for the formula I and $R_{2'}$ represents an alkyl radical having 1 to 6 carbon atoms or a benzyl radical, which compounds are then either reacted with ethyl chloroformate to form the compounds of formula V in which $R_1$ represents a dihydronaphthyl radical of formula $y_2$, A is a single bond and B represents a piperidyl radical, or subjected to the action of tetrachloro-1,2-benzoquinone to form the compounds of formula $I_f$:

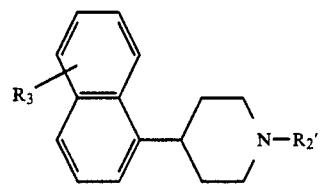
(If)

in which $R_3$ has the same meaning as for the formula I and $R_{2'}$ represents an alkyl radical having 1 to 6 carbon atoms or a benzyl radical, which compounds are then reacted with ethyl chloroformate to form the compounds of formula V in which $R_1$ represents a naphthyl radical of formula $y_1$, A is a single bond and B represents a piperidyl radical, and then the compounds of formula V are subjected either to the action of hydrobromic acid or to the action of potassium hydroxide, to form the compounds of formula Ig:

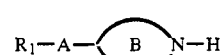
(Ig)

in which the meaning of $R_1$, A and B remains identical to that given for the formula I, which compounds are then reacted with a compound of formula XII:

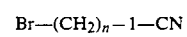     (XII)

in which n has the same meaning as for the formula I, to form the compounds of formula $I_h$:

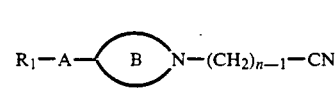
(Ih)

in which $R_1$, A, B and n have the same meaning as for the formula I, which compounds are then subjected to the action of lithium aluminum hydride to form the compounds of formula $I_i$:

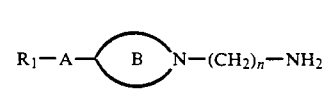
(Ii)

in which the meaning of $R_1$, A, B and n remains identical to that given for the formula I, which compounds are reacted with a compound of formula XIII:

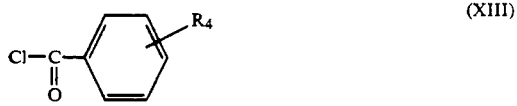

in which the meaning of $R_4$ remains identical to that given for the formula I, to form the compounds of formula $I_j$:

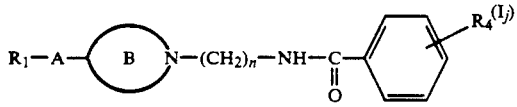

in which $R_1$, A, B, n and $R_4$ have the same meaning as for the formula I, and then the compounds of formula $I_a$-$I_j$ (which make up all of the compounds of formula I) are separated into their possible stereoisomers, and/or the said compounds are converted to a salt with a pharmaceutically acceptable organic or inorganic acid, to form the corresponding addition salts.

The reaction of the compounds of formula II with the compounds of formula III is carried out in the presence of butyllithium, in tetrahydrofuran or some other chemically equivalent solvent, and at a temperature of between −60° C. and −78° C.

Preferentially, the catalyst used during the hydrogenation of the compounds of formula $I_a$ to form the compounds of formula $I_b$ is palladium-on-charcoal.

During the reaction of the compounds of formulae Ia, $I_b$, $I_c$, $I_d$, $I_e$ and $I_f$ with ethyl chloroformate, the alkali metal inorganic salt used is sodium bicarbonate.

The reaction of the compounds of formula VI with the compounds of formula VII is carried out in the presence of the titanium trichloride/dimethoxyethane complex and the zinc-copper system (prepared by the process described in J.Org.Chem. (1989), 54, p. 3749).

The reaction of the compounds of formula IX and XI with para-toluenesulfonic acid is carried out at elevated temperature, in dichloromethane or in some other halogenated aliphatic solvent of low molecular weight ($C_1$-$C_3$).

In order to form the compounds of formula $I_f$, the oxidation of the compounds of formula Ie is carried out using tetrachloro-1,2-benzoquinone, at elevated temperature, in an anhydrous alcoholic solvent.

In order to form the compounds of formula $I_g$, the compounds of formula V are subjected at elevated temperature either to the action of potassium hydroxide in solution in ethanol or to the action of 48% hydrobromic acid.

The reaction of the compounds of formula $I_i$ with the compounds of formula XIII is carried out at ambient temperature.

Amongst the pharmaceutically acceptable acids for the preparation of the addition salts with compounds of general formula I, the following may be mentioned: hydrochloric, phosphoric, fumaric, citric, oxalic, sulfuric, ascorbic, tartaric, maleic, mandelic and methanesulfonic acids, etc.

The compounds of the present invention have very valuable pharmacological properties. On the cardiovascular level, the compounds of the invention lower the arterial pressure and the heart rate in rats and in dogs. This action results from a central inhibition of the sympathetic tonus. In fact, pharmacological studies have shown that the lowering in pressure caused by the i.v. administration of the compounds of the invention to dogs is accompanied by a significant reduction in the electrical activity of the renal sympathetic nerve.

This central reduction in the sympathetic tonus results from an activation Of the central 5-$HT_{1A}$ receptors at the level of the retrofacial nucleus (Eur. Journal of Pharm., (1989,160,p.385-294). Pharmacological studies have also proved that the compounds of the invention are more active than flesinoxan, a reference compound having antihypertensive properties owing to its agonist activity on the 5-$HT_{1A}$ receptors (European Journal of Pharmacology, (1988),149,p.213-223). On the other hand, the compounds of the invention have a beneficial activity at the renal level (T.I.P.S., (1989), 10, p.469-471).

Binding studies have confirmed that the compounds of the invention also behave as very powerful ligands for 5-$HT_{1A}$ receptors, with an agonist or antagonist activity on the central nervous system.

The compounds of the invention therefore find their application in the treatment of stress (Neuropharmac.,(1989), Vol.25, No.5, p.471-476), migraine (T.I.P.S., (1989), Vol.10, pp.200-204) anxiety, depression, schizophrenia and pain (Pharmacology and Toxicology, (1989), 64, p.3-5), (Drugs of the Future, (1988), 13, No.5, p.429-437), (J. Neural. Transm., (1988), 74, p.195-198).

The compounds which are active at the level of the 5-$HT_{1A}$ receptors may also modify the alimentary and sexual behavior (Jour. of Receptor Research, (1988), 8, p.59-81).

The invention also extends to the pharmaceutical compositions containing, as active principle, at least one compound of general formula I, or one of its salts with a pharmaceutically compatible inorganic or organic acid, in combination with one or more inert and suitable excipients.

The pharmaceutical compositions thus obtained are advantageously presented in diverse forms, such as, for example, tablets, coated tablets, capsules, suppositories, injectable solutions or drinkable solutions.

The dosage may vary widely depending on the age and the weight of the patient, on the nature and the severity of the illness and on the administration route. In general, the unit dose will range between 0.1 and 100 mg and the daily dose, usable in human medicine, between 0.1 and 500 mg. The preferred administration route is the oral or parenteral route.

The following examples, given without any limitation being implied, illustrate the invention.

The melting points were measured using the Micro-Köfler technique.

The proton nuclear magnetic resonance (1H NMR) spectra of the compounds of general formula I were recorded, depending on the case, at 200 and 400 MHz and are indicated in Table I.

EXAMPLE 1

1-Methyl-4 (naphth-1-yl) 1,2,3,6 tetrahydropyridine hydrobromide

Stage A

4-Hydroxy-1 methyl-4-(naphth 1-yl)piperidine

A solution of 51.75 g of 1-bromonaphthalene in 250 ml of tetrahydrofuran is added dropwise, at −78° C. and under a stream of nitrogen, to a solution of 175 ml of butyllithium (1.6 M in hexane) in 500 ml of tetrahydrofuran.

After stirring for 1 hour, a solution of 28.29 g of 1-methylpiperid-4-one in 250 ml of tetrahydrofuran is added dropwise.

The reaction mixture is stirred for 1 hour at −78° C. and then for 5 hours at 20° C. and is then hydrolyzed with 100 ml of a saturated ammonium chloride solution.

Extraction with dichloromethane followed by evaporation of the solvent leaves an oily residue which, taken up in ethyl ether, crystallizes in the form of a white solid.

Yield: 73 %
Melting point : 160° C.

Proton nuclear magnetic resonance spectrum (solvent CDCl$_3$): 2.2 ppm s+m 3H+4H; 2.65 ppm m 4H; 7.35 ppm m 4H; 7.75 ppm d 1H; 7.85 ppm m 1H; 8.9 ppm m 1H.

Stage B 49 g of the compound obtained in the preceding stage, in suspension in 1 liter of a 48% hydrobromic acid solution, are refluxed for 24 hours. The residue obtained after evaporation is taken up 3 times with ethanol and then with acetone to yield, after filtration and drying, 47.94 g of 1-methyl-4-naphth-1-yl-1,2,3,6-tetrahydropyridine hydrobromide.

Yield : 86.65%
Melting point : >260° C.

EXAMPLE 2

1 Methyl-4-naphth-1-ylpiperidine hydrobromide 20 g of the compound from Example 1 are reduced with 1680 ml of hydrogen under atmospheric pressure and at ambient temperature, in the presence of 1 g of 10% palladium-on-charcoal, in 1 liter of ethanol and 100 ml of dimethylformamide.

After filtering off the catalyst and evaporation of the solvents, a crude product is obtained which when taken up in acetone yields 19 g of the expected hydrobromide.

Yield : 95.5%
Melting point : >260° C.

EXAMPLE 3

4-Naphth-1-ylpiperidine hydrobromide

Stage A

Ethyl [4-(naphth-1 Yl)piperid-1-yl]carbamate 19 g of the salt obtained in Example 2 are converted to 1-methyl-4-naphth-1-ylpiperidine using sodium hydroxide in dichloromethane.

The base thus obtained is immediately brought into contact with 10 g of sodium bicarbonate in 500 ml of toluene, under a stream of nitrogen. 100 ml of ethyl chloroformate are added in fractions to the reaction mixture and the whole is then refluxed for 24 hours. Filtration followed by evaporation leads to 10.7 g of an oil.

Yield: 61.14%

Stage B 10.5 g of the compound obtained in Stage A in 300 ml of a 48% hydrobromic acid solution, are refluxed for 20 hours. After evaporation and washing twice with ethanol, the residue is taken up in acetone and the mixture then filtered to give 4-(naphth-1-yl)pyperidine hydrobromide.

Yield: 86.64%
Melting point: >260° C.

EXAMPLE 4

(4-Naphth-1-ylpiperid-1-yl)acetonitrile hydrochloride 5 g of the compound from Example 3, 7.088 g of potassium carbonate and 2.259 g of bromoacetonitrile in 200 ml of acetone are stirred for 10 hours under reflux and a stream of nitrogen. After filtering and evaporation of the filtrate, the residue obtained is treated with an ethanolic solution of hydrogen chloride to give 4.5 g of the expected hydrochloride.

Yield: 91.83%
Melting point: 172° C.

EXAMPLE 5

1-[2-(4-Fluorobenzamido)eth-1-yl]-4-naphth-1-ylpiperidine hydrochloride

Stage A 1-(2-Aminoeth-1-yl)-4-naphth-1-ylpiperidine 1.75 g of lithium aluminum hydride are added in fractions under a stream of nitrogen to a solution of 4.4 g of the compound from Example 4 in 150 ml of tetrahydrofuran. After stirring for 1 hour, the mixture is hydrolyzed with 1.75 ml of water, 3.5 ml of a 10% (wt/wt) sodium hydroxide solution and 7 ml of water. Filtration through celite, followed by evaporation of the solvent, yields an oily product which is used as it is in the following stage.

Yield: quantitative

Stage B

A solution of 1.81 g of triethylamine in 40 ml of tetrahydrofuran is added dropwise at −5° C., under a stream of nitrogen, to a solution of 3.8 g of the compound obtained in the preceding stage, in 180 ml of tetrahydrofuran. Under the same conditions, a solution of 2.84 g of 4-fluorobenzoyl chloride in 40 ml of tetrahydrofuran is added to the reaction mixture. After having stirred for 1 hour at ambient temperature, the mixture is hydrolyzed using a saturated sodium bicarbonate solution. Phase separation, followed by drying of the organic phase over sodium sulfate and the evaporation of the solvent leads to a product which, when taken up in ethyl ether, crystallizes in the form of a white solid.

3.3 g of the corresponding hydrochloride are obtained after addition of an ethanolic solution of hydrogen chloride.

Yield: 64%
Melting point: 260° C.

EXAMPLE 6

1-[2-(4-Fluorobenzamido)eth-1-yl]-4-naphth-1-yl-1,2,3,6-tetrahydropyridine hydrochloride

Stage A

Ethyl (4-naphth-1-yl-1,2,3,6-tetrahydropyrid-1-yl)carbamate 22.3 g of the compound from Example 1 are treated with 50 ml of ethyl chloroformate and 30 g of sodium bicarbonate, in accordance with the procedure described in Stage A of Example 3, to give the expected product.

Yield: 53.88%

Proton nuclear magnetic resonance spectrum (solvent $CDCl_3$): 1.3 ppm t 3H; 2.55 ppm m 2H 3.8 ppm m 2H 4.1–4.3 ppm g+m+m 2H+1H+1H; 5.8 ppm m 1H; 7.25 ppm dd 1H; 7.35–7.55 ppm m 3H; 7.7–8 ppm m+d 2H+1H.

Stage B

4-Naphth-1-yl-1,2,3,6-tetrahydropyridine hydrobromide

The treatment of 11 g of the carbamate obtained in the preceding stage with a 48% hydrobromic acid solution yields 9.02 g of 4-naphth-1-yl-1,2,3,6-tetrahydropyridine hydro bromide.

Yield: 80%

Melting point: >260° C.

Stage C (4-Naphth-1-yl-1,2,3,6 tetrahydropyrid-1-yl)acetonitrile hydrochloride This salt was obtained from the compound obtained in Stage B using the process described in Example 4.

Yield: 80%

Stage D 1-(2-Aminoeth-1-yl)-4-naphth-1-yl-1,2,3,6-tetrahydropyridine 6.25 g of the hydrochloride prepared previously are reduced using 2.5 g of lithium aluminum hydride and yield the expected amino compound, which is used immediately in the following stage.

Yield: quantitative

Stage E

The treatment of 5.5 g of the amine prepared in the preceding stage with 2.66 g of triethylamine and 4.18 g of 4-fluorobenzoyl chloride leads to a crude product which is purified by chromatography on a silica gel column (70–230 mesh) using a 97: 3: 0.3 (V/V/V) mixture of dichloromethane, methanol and aqueous ammonia as the elution solvent.

The product thus obtained is converted to the hydrochloride.

Yield: 37%

Melting point: 233° C.

EXAMPLE 7

3-(1-Methyl-1,2,3,6-tetrahydropyrid-4-yl)quinoline dihydrobromide

Stage A 3-(4-Hydroxy 1-methylpiperid 4-yl)quinoline 95.01 g of 3-bromoquinoline were treated with 200 ml of a 2.5 M solution of butyllithium in hexane and 51.62 g of 1-methylpiperid-4-one in accordance with the procedure described in Stage A of Example 1, in order to obtain the expected product.

Yield: 53.84%

Melting point: 175° C.

Proton nuclear magnetic resonance spectrum (solvent $CDCl_3$): 2.3 ppm t+d 2H; 2.4 ppm s 3H; 2.55 pp t+d 2H; 2.85 ppm d 2H; 7.7 and 7.55 ppm m+m 2H; 7.8 ppm d 1H; 8.10 ppm d 1H; 8.25 ppm d 1H; 9.1 ppm d 1H.

Stage B

The 3-(1-methyl-1,2,3,6-tetrahydropyrid-4-yl)quinoline dihydrobromide was obtained by treating 53 g of the compound obtained in Stage A with a 48% hydrobromic acid solution.

Yield: 72.80%

Melting point: >260° C.

EXAMPLE 8

3-(1,2,3,6-Tetrahydropyrid-4-yl)quinoline hydrochloride

This product was prepared from the compound of Example 7 and using the procedure described in Stages A and B of Example 6. The compound obtained was converted to a salt using an alcoholic solution of hydrogen chloride.

Yield: 65%

Melting point: >260° C.

EXAMPLE 9

3-(1-Methylpiperid-4-yl)quinoline dihydrobromide

Hydrogenation of the compound of Example 7, in accordance with the procedure described in Example 2, yields the expected compound.

Yield: 95.4%

Melting point: >260° C.

EXAMPLE 10

3-Piperid-4-ylquinoline dihydrobromide

This product was prepared from the compound of Example 9 using the procedure described in Example 3.

Yield: 74%

Melting point: >260° C.

EXAMPLE 11

[4-(Quinol-3-yl)piperid-1-yl]acetonitrile dihydrochloride

The treatment of 10.90 g of the compound from Example 10 with 2.3 ml of bromoacetonitrile and 16 g of potassium carbonate yields 9.08 g of the expected product, in the form of the base. An ethanolic solution of hydrogen chloride is used for conversion to the salt.

Yield: 85.77%

Melting point: 210°–214° C.

EXAMPLE 12

1-[2-(4-Fluorobenzamido)eth-1-yl]-4-quinol-3-ylpiperidine dihydrochloride

This product was prepared from the compound of Example 11 and in accordance with the procedure described in Example 5.

Yield: 50%

Melting point: 229° C.

EXAMPLE 13

1-Benzyl-3-[3,4-dihydro-7-methoxynaphth-1-yl)methylenyl]pyrrolidine

Stage A

1-Benzyl-3-[(1-hydroxy-7-methoxy-1,2,3,4-tetrahydronaphth-1-yl)methylenyl]pyrrolidine 40 g of 3-chloromethyl-1-benzyl pyrrolidine are added under nitrogen to a suspension of 4.63 g of magnesium in 100 ml of anhydrous ethyl ether.

The reaction mixture is diluted little by little with 300 ml of benzene at the rate at which the magnesium disappears. The mixture is refluxed for 1 hour and then cooled to 0° C. and a solution of 37 g of 7-methoxy-1,2,3,4-tetrahydronaphth-1-one in 120 ml of benzene is added.

The temperature is allowed to rise to 20° C. and after 36 hours the mixture is hydrolyzed with 200 ml of a saturated ammonium chloride solution.

After drying and concentrating the organic phase, the oil obtained is purified by chromatography on silica using a 100 3 (V/V) mixture of dichloromethane and methanol as eluent.

Yield: 48%

Proton nuclear magnetic resonance spectrum (solvent $CDCl_3$): 1.65 to 2.1 ppm m+m+m+d+dd 1H+2H+2H+2H+1H; 2.15 to 2.5 ppm m+m+m 1H+1H+1H; 2.6 to 2.85 ppm m+m+dd 2H+1H+1H; 3.55 ppm dd 2H; 3.75 ppm s 3H; 6.7 ppm dd 1H; 7.0 ppm d 1H; 7.05 ppm d 1H; 7.1 to 7.4 ppm m 5H.

Stage B

A solution of 20 g of the product obtained in Stage A and 11.9 g of para-toluenesulfonic acid monohydrate in 600 ml of dichloromethane is refluxed for 30 minutes.

The amine is then salted out using a sodium hydroxide solution and the organic phase is concentrated. The oil obtained is purified by chromatography on silica (70–230 mesh) using a 3:100 (V/V) mixture of methanol and dichloromethane as eluent.

12 g of 1-benzyl-3-[3,4-dihydro-7-methoxynaphth-1-yl) methylenyl]pyrrolidine are thus obtained.

EXAMPLE 14

1-Benzyl-3-[(7 methoxy-1,2,3,4-tetrahydronaphth-1-yl) methylidyn]pyrrolidine 3 g of this compound were obtained on purification, by chromatography, of the oil obtained in Stage B of Example 13.

EXAMPLE 15

4-(3,4-Dihydro-7-methoxynaphth-1-yl)-1 methylpiperidine

Stage A 4-(1-Hydroxy-7-methoxy-1,2,3,4-tetrahydronaphth-1-yl)-1-methylpiperidine A solution of 40 g of 4-chloro-1-methylpiperidine in 150 ml of tetrahydrofuran is added to a suspension of 6.9 g of magnesium in 50 ml of tetrahydrofuran.

The formation of the magnesium compound is completed by refluxing for 2 hours.

A solution of 32.2 g of 7-methoxy-1,2,3,4-tetrahydronaphth-1-one in 150 ml of tetrahydrofuran is then added at 10° C.

Stirring of the reaction mixture is continued at ambient temperature for 15 hours and the mixture is then hydrolyzed at 0° C. using 15 g of ammonium chloride in solution in 80 ml of water.

After evaporation of the solvent under vacuum, the residue is taken up in water, the mixture is acidified and washed with ethyl ether, the aqueous phase is then rendered alkaline and the product extracted with 400 ml of toluene is washed with 200 ml of water.

After concentration under vacuum, the oil obtained crystallizes.

Melting point: >60° C.

Stage B

A solution of 15 g of the oil obtained in Stage A, in 400 ml of anhydrous dichloromethane, is refluxed for 20 minutes in the presence of 11.4 g of para-toluenesulfonic acid.

After cooling, the reaction mixture is washed with 20 ml of a saturated sodium bicarbonate solution. The organic phase is dried over sodium sulfate and then concentrated under vacuum. An oil is obtained.

Yield: 40%

EXAMPLE 16

4-(7-Methoxynaphth-1-yl)-1-methylpiperidine

A mixture of 11.5 g of the product from Example 15 and 23.1 g of tetrachloro-1,2-benzoquinone in solution in 600 ml of anhydrous ethyl alcohol is refluxed for 30 hours.

After concentration under vacuum, the residue is taken up in water and then extracted with dichloromethane and the extract is dried over anhydrous sodium sulfate and concentrated under vacuum.

The product obtained is purified on a neutral alumina column using a 99.5:0.5 (V/V) mixture of dichloromethane and methanol.

Yield: 82%

EXAMPLE 17

4-(7-Methoxynaphth-1-yl)piperidine hydrochloride

Stage A

Ethyl 4-(7-methoxynaphth-1-yl)piperid-1-yl]carbamate

The compound of Example 16 is dissolved in 200 ml of anhydrous xylene in the presence of 3.9 g of sodium carbonate and 17.6 ml of ethyl chloroformate are added at 20° C. The mixture is refluxed for 24 hours.

The reaction mixture is cooled and then hydrolyzed using a 2 N hydrochloric acid solution.

The organic phase is washed with a dilute sodium hydroxide solution, dried over sodium sulfate and concentrated under vacuum.

Yield: 88%

Stage B

A mixture of 8.9 g of the carbamate obtained in Stage A, 12.7 g of potassium hydroxide, 30 ml of water and 200 ml of ethyl alcohol is refluxed for 40 hours.

After evaporation under vacuum, the residue is taken up in water and the mixture is extracted with dichloromethane.

The organic phase is dried over sodium sulfate and concentrated under vacuum.

The oil obtained is converted to the salt using 3.12 ml of a 7.6 N ethanolic solution of hydrogen chloride.

Yield: 55%

Melting point: 240° C.

EXAMPLE 18

1-[2-(4-Fluorobenzamido)eth-1-yl]-4-(7-methoxynaphth-1-yl) piperidine hydrochloride This product was prepared from the compound of Example 17 and using successively the procedures described in Examples 4 and 5.

Yield: 25%
Melting point: 215° C.

EXAMPLE 19

4-(7-Methoxy-1,2,3,4 tetrahydronaphth-1-yl)piperid-4-ylidene

Stage A

Ethyl [4-(7-methoxy-1,2,3,4-tetrahydronaphth-1-yl)piperid-4-ylidene]carbamate 921 g of the 1 M 1.5 M titanium trichloride/dimethoxyethane complex and then 888 g of the zinc/copper system (prepared by the process described by J. McMurry. J. Org. Chem. (1989), 54, p. 3749) are poured successively, under a stream of argon, into 8 liters of dimethoxyethane. The mixture is refluxed for 13 hours and then cooled to 20° C.

A solution consisting of 31 g of 7-methoxy-1,2,3,4-tetrahydronaphth-1-one, 60.3 g of ethyl (4-oxopiperid-1-yl)carbamate and 400 ml of dimethoxyethane is added dropwise in the course of 5 hours to the reaction mixture. The latter is then refluxed again for 15 hours, then cooled and diluted with 3 liters of dichloromethane.

After filtering through celite and concentrating the filtrate under vacuum, the residue obtained is taken up in 800 ml of dichloromethane.

The insoluble matter is removed by filtering off and the organic phase is evaporated under vacuum.

The oil obtained is purified by chromatography on a silica column using dichloromethane as eluent.

Yield: 55%

Proton nuclear magnetic resonance spectrum (solvent CDCl$_3$): 1.25 ppm t 3H; 1.75 ppm q 2H; 2.45 ppm m 4H; 2.6 ppm t 2H; 2.65 ppm t 2H; 3.4 ppm t 2H; 3.55 ppm t 2H; 3.8 ppm s 3H; 4.2 ppm q 2H; 6.7 ppm m 2H; 7.0 ppm d 1H.

Stage B 2.6 g of the compound obtained in Stage A were treated by the procedure described in Stage B of Example 17 in order to obtain the expected salt.

Yield: 63%
Melting point: >260° C.

EXAMPLE 20

[4-(7 Methoxy-1,2,3,4-tetrahydronaphth-1-yl)piperid-4-ylidene]acetonitrile

This compound was prepared from the compound of Example 19 using the procedure described in Example 4.

Yield: 94%

EXAMPLE 21

1-[2-(4-Fluorobenzamido)eth-1-yl]-4-(7-methoxy-1,2,3,4-tetrahydronaphth-1-yl)piperid-4-ylidene hydrochloride This compound was prepared from the compound of Example 20 using the procedure described in Example 5.

Yield: 80%
Melting point: 120° C.

EXAMPLE 22

1-Benzyl-4-(1,4-benzodioxan-5-yl)-1,2,3,6-tetrahydropyridine

Stage A

1-Benzyl-4-hydroxy-4-(1,4-benzodioxan-5-yl)piperidine 23.3 ml of a 1.6 M solution of butyllithium in hexane are added dropwise to a solution, previously cooled to −60° C., of 8 g of 5-bromo-1,4-benzodioxane in 400 ml of tetrahydrofuran. When the addition is complete, the mixture is stirred at −60° C. for 5 minutes and a solution of 8 g of 1-benzylpiperid-4-one in 100 ml of tetrahydrofuran is then added dropwise. The mixture is stirred for 2 hours at −40° C. and then for 2 hours at ambient temperature before hydrolyzing using 80 ml of water.

The organic phase is separated off and the aqueous phase is extracted with twice 100 ml of dichloromethane. The combined organic phases are washed once using 20 ml of water and dried over magnesium sulfate.

The solvents are evaporated under vacuum and the product obtained in the crude stage is chromatographed on 520 of silica (70–230 mesh), eluting using a 98:2 (V/V) dichloromethane/methanol mixture.

Yield: 72%

Proton nuclear magnetic resonance spectrum (solvent CDCl$_3$): 2.05 ppm m 2H; 2.1 ppm m 2H; 2.55 ppm m 2H; 2.75 ppm m 2H; 3.6 ppm s 2H; 4.25 ppm m 4H; 6.8 ppm m 3H; 7.1-7.4 ppm m 5H

Stage B

A solution of 8 g of the product obtained in the preceding stage, in 100 ml of glacial acetic acid and 8 ml of concentrated hydrochloric acid, is refluxed for 14 hours.

After returning to ambient temperature, the mixture is concentrated and the residue is taken up using 250 ml of dichloromethane.

The separated organic phase is washed once using 80 ml of 1 N sodium hydroxide and then once using 80 ml of water.

After drying over magnesium sulfate and concentrating under vacuum, an oil is obtained.

Yield: 74%

EXAMPLE 23

4-[5-(1,4-Benzodioxan-5-yl)]-1-[2-(4-fluorobenzamido)eth-1-yl]-1,2,3,6-tetrahydropyridine hydrochloride

Stage A

Ethyl [4-(1,4-benzodioxan-5-yl)-1,2,3,6-tetrahydropyrid-1-yl]carbamate 8 g of ethyl chloroformate are added at ambient temperature, with stirring, to a solution containing 5.5 g of the product from Example 22 in 50 ml of toluene. When the addition is complete, the mixture is refluxed for 2 hours.

The cooled solution is filtered, the filtrate is concentrated under vacuum and the residue is taken up in 250 ml of a 50:50 (V/V) mixture of ethyl ether and diisopropyl ether. The precipitate is filtered off and the filtrate is concentrated in order to obtain an oil.

Yield: 63%

Proton nuclear magnetic resonance spectrum (solvent $CDCl_3$):

1.3 ppm t 3H; 2.5 ppm m 2H; 3.65 m 2H; 4–4.30 ppm m 2H; 4.10 ppm s 4H; 4.35 ppm q 2H; 5.8 ppm m 1H; 6.6–6.8 ppm m 3H

Stage B

4-[(1,4-Benzodioxan-5-yl)]-1,2,3,6-tetrahydropyridine hydrochloride 1.7 ml of trimethylsilane iodide are added dropwise to a solution of 3 g of the carbamate obtained in the preceding stage, in 4.2 ml of chloroform. When the addition is complete, the mixture is stirred for 1 hour under reflux and then for 2 hours at ambient temperature.

The mixture is filtered rapidly, the filtrate is diluted using 20 ml of chloroform, 10 ml of a methanolic solution of hydrogen chloride are then added dropwise and the mixture is diluted using 30 ml of ethyl ether. The precipitate formed is the expected product.

Yield: 77%

Melting point: 184° C. (decomposition)

Stage C

[4-(1,4-Benzodioxan-5-yl)-1,2,3,6-tetrahydropyrid-1-yl]acetonitrile 2.5 g of potassium carbonate and, dropwise, a solution of 1.08 g of bromoacetonitrile in 10 ml of acetone are added to a solution of 1.9 g of the amine hydrochloride obtained in Stage B in 40 ml of acetone.

The mixture is stirred for 2 hours at ambient temperature and filtered and the filtrate is concentrated under vacuum. The residue, taken up in 20 ml of dichloromethane, is washed using 10 ml of water and the organic phase is then dried over magnesium sulfate.

After evaporation of the solvent, an oil is obtained.
Yield: 99%

Proton nuclear magnetic resonance spectrum (solvent $CDCl_3$): 2.6 ppm m 2H; 2.8 ppm t 2H; 3.3 ppm m 2H; 3.65 ppm s 2H; 4.2 ppm s 4H; 5.8 ppm m 1H; 6.75 ppm m 3H

Stage D 1-(2-Aminoethyl)-4-(1,4-benzodioxan-5-yl)-1,2,3,6-tetrahydropyridine A solution containing 1.9 g of the compound obtained in Stage C, in 20 ml of anhydrous tetrahydrofuran, is added dropwise to a suspension of 0.56 g of lithium aluminum hydride in 30 ml of anhydrous tetrahydrofuran.

After 4 hours' contact at ambient temperature, the mixture is hydrolyzed using 0.6 ml of a saturated ammonium chloride solution.

The mixture is filtered and the filtrate is dried over magnesium sulfate.

After concentration of the solvent, an oil is obtained which is used as such in the following step.

Stage E

All of the compound obtained in Stage D is dissolved in 20 ml of chloroform. A solution of 0.64 g of triethylamine in 5 ml of chloroform and then, dropwise, a solution of 0.94 g of para-fluorobenzoyl chloride in 30 ml of chloroform are added thereto.

After 3 hours' contact, the mixture is washed once using 10 ml of water and the organic phase is dried over magnesium sulfate and then concentrated under vacuum.

The crude oil is dissolved in 50 ml of ether and the product is precipitated by adding an ethereal solution of hydrogen chloride.

The precipitate filtered off is taken up in 20 ml of ether. A solid is thus obtained which is the expected salt.

Yield: 68%

Melting point: 214° C.

EXAMPLE 24

[4-(3,4-Dihydro-7-methoxynaphth-1-yl)piperid-1-yl]acetonitrile

Stage A

Ethyl[4-(3,4-dihydro-7-methoxynaphth-1-yl)piperid-1-yl]carbamate

The expected product is obtained using the compound from Example 15 and treating it in accordance with the procedure described in Stage A of Example 3.

Yield: 93%

Stage B 4-(3,4-Dihydro-7-methoxynaphth-1-yl)piperidine

The expected product is obtained using the compound described in Stage A and treating it in accordance with the procedure described in Stage B of Example 17.

Yield: 77%

Stage C

[4-(3,4-Dihydro-7-methoxynaphth-1-yl)]piperid-1yl-]acetonitrile

The expected product is obtained using the compound described in Stage B and treating it in accordance with the procedure described in Example 4.

Yield: 92%

| | Elementary microanalysis: | | |
|---|---|---|---|
| | C % | H % | N % |
| Calculated | 76.56 | 7.85 | 7.79 |
| Found | 75.50 | 9.92 | 9.57 |

EXAMPLE 25

1-(2-Aminoeth-1-yl)-4-(3,4-dihydro-7-methoxynaphth-1-yl) piperidine

The expected product is obtained using the compound from Example 24 and treating it in accordance with the process described in Stage A of Example 5.

Yield: 81%

EXAMPLE 26

1-(2-Aminoeth 1-yl)
4-(1,2,3,4-tetrahydro-7-methoxynaphth-1-yl)piperidine 900 mg of the compound described in Example 25 are reduced by catalytic hydrogenation at ambient temperature in the presence of 0.1 g of platinum oxide in 10 ml of acetic acid. The expected product is obtained after filtering off the catalyst, neutralizing the filtrate with sodium hydroxide solution and extracting with dichloromethane.

Yield: =100%

| | Elementary microanalysis: | | |
|---|---|---|---|
| | C % | H % | N % |
| Calculated | 74.96 | 9.78 | 9.71 |
| Found | 74.99 | 9.83 | 9.27 |

EXAMPLE 27

1-[2-(4-Fluorobenzamido)eth-1-yl]-4-(3,4-dihydro-7-methoxynaphth-1-yl)piperidine hydrochloride The expected product is obtained in the form of the base using the compound from Example 25 and treating it in accordance with the procedure described in Stage B of Example 5. The base is converted to the corresponding hydrochloride by treatment with an alcoholic solution of hydrogen chloride.

Yield: 65%
Melting point: 250° C.

| | Elementary microanalysis: | | | |
|---|---|---|---|---|
| | C % | H % | N % | Cl % |
| Calculated | 67.48 | 6.80 | 6.30 | 7.97 |
| Found | 67.36 | 6.78 | 6.23 | 7.95 |

EXAMPLE 28

1-[2-(4-Fluorobenzamido)eth-1-yl]-4-(1,2,3,4-tetrahydro-7-methoxynaphth-1-yl)piperidine hydrochloride The expected product is obtained in the form of the base using the compound from Example 26 and treating it in accordance with the procedure described in Stage B of Example 5. The base is converted to the corresponding hydrochloride by treatment with an alcoholic solution of hydrogen chloride.

Yield: 42%
Melting point: 204° C.

| | Elementary microanalysis: | | | |
|---|---|---|---|---|
| | C % | H % | N % | Cl % |
| Calculated | 67.18 | 7.22 | 6.27 | 7.93 |
| Found | 67.36 | 7.24 | 6.42 | 7.87 |

EXAMPLE 29

1-Benzyl-3-[(7-methoxynaphth-1-yl)methyl]pyrrolidine 64 mmoles of the compound obtained in Stage B of Example 13 are refluxed in 220 ml of anhydrous ethanol in the presence of 19 g of o-chloranil and 8.5 ml of a 7.6 N ethanolic hydrochloric acid solution.

After evaporation, the residue is taken up in water, the whole is brought to pH 10 and filtered through celite and the filtrate is extracted with dichloromethane.

The expected product is obtained after drying and evaporating off the solvents and is purified by chromatography on silica (elution solvent: dichloromethane/methanol/aqueous ammonia 99:1:0.1).

Yield: 70%

EXAMPLE 30

3-[7-Methoxynaphth-1-yl)methyl]pyrrolidine

The expected product is obtained by catalytic hydrogenation of the compound from Example 29° at 60° C. in ethanol in the presence of 1.5 g of palladium-on-charcoal.

Yield: 85%

EXAMPLE 31

1-Cyanomethyl-3-[(7-methoxynaphth-1-yl)methyl]pyrrolidine

The expected product is obtained using the compound from Example 30 and treating it in accordance with the procedure described in Example 4 without conversion to the hydrochloride.

Yield: 95%

EXAMPLE 32

1-(2-Aminoeth-1-yl)-3-[(7-methoxynaphth-1-yl)methyl]pyrrolidine

The expected product is obtained using the compound from Example 31 and treating it in accordance with the procedure described in Stage A of Example 5.

Yield: 65%

EXAMPLE 33

1-[2-(4-Fluorobenzamido)eth-1-yl]-3-[(7-methoxynaphth-1-yl) methyl]pyrrolidine

The expected product is obtained using the compound from Example 32 and treating it in accordance with the procedure described in Stage B of Example 5.

Yield: 80%
Melting point: >260° C.

| | Elementary microanalysis: | | |
|---|---|---|---|
| | C % | H % | N % |
| Calculated | 65.31 | 5.89 | 5.64 |
| Found | 64.99 | 5.72 | 5.99 |

TABLE I

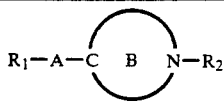

| Example No. | R₁ | A | B | R₂ | NMR SPECTRUM (Solvent) s = salt b = base |
|---|---|---|---|---|---|
| 1 | naphthyl | — | 1,2,3,6-tetrahydropyridin-4-yl (N-) | —CH₃ | ¹H NMR (DMSO-d₆) s 2.75ppm m 2H; 2.95ppm s 3H; 3.5ppm m 2H; 3.95 ppm m 2H; 5.75ppm m 1H; 7.35ppm dd 1H; 7.55 ppm m 3H; 7.9ppm d 1H; 8ppm m 1H; 8.05 ppm m 1H; 9.5-10.5ppm 1H (exchangeable) |
| 2 | naphthyl | — | piperidin-4-yl (N-) | —CH₃ | ¹H NMR (DMSO-d₆) s 2-2.2ppm m 4H; 2.8ppm s 3H; 3.3ppm m 2H; 3.6 ppm m 2H; 3.7ppm m 1H; 7.3-7.7ppm m +d 3H+1H; 7.85ppm d 1H; 7.95ppm dd 1H; 8.2ppm dd 1H; 9.2-10.2 ppm 1H exchangeable |
| 3 | naphthyl | — | piperidin-4-yl (N-) | H | ¹H NMR (DMSO-d₆) s 1.9-2.15ppm m 4H; 3.1-3.6ppm m 4H; 3.8ppm m 1H; 7.3-7.65ppm m+t+d 2H+1H+1H; 7.8ppm d 1H; 7.95ppm m 1H; 8.3ppm m 1H; 8.4-9 ppm 1H exchangeable |
| 4 | naphthyl | — | piperidin-4-yl (N-) | —CH₂CN | ¹H NMR (DMSO-d₆) s 2-2.4ppm m 4H; 3.2-3.9 ppm m+m+m 1H+2H+2H; 4.6ppm s 2H; 7.25-7.65ppm m+d 3H+1H; 7.8ppm d 1H; 7.9ppm dd 1H; 8.25ppm dd 1H |
| 5 | naphthyl | — | piperidin-4-yl (N-) | —(CH₂)₂—NH—C(O)—C₆H₄—F | ¹H NMR (DMSO-d₆) s 1.8-2.4ppm m 4H; 3-3.5 ppm m 4H; 3.5-4ppm m 5H; 7.2-7.7ppm m+m+t 3H+1H+2H; 7.8ppm d 1H; 7.85-8.15 ppm dd+m 2H+1H; 8.2 ppm d 1H; 8.8-9.3ppm 1H exchangeable; 10.4-10.7ppm 1H exchangeable |
| 6 | naphthyl | — | 1,2,3,6-tetrahydropyridin-4-yl (N-) | —(CH₂)₂—NH—C(O)—C₆H₄—F | ¹H NMR (DMSO-d₆) s 2.5-2.7ppm m 1H; 2.9-3.2ppm m 1H; 3.3-3.6 ppm m+m 2H; 3.7-4.05 ppm m+t 2H+2H; 4.2 ppm m 1H; 5.75ppm m 1H; 7.25-7.40ppm m 3H; 7.45-7.60ppm m 3H; 7.8-8.0ppm m+m 1H+1H; 8.05-8.3ppm m+dd 1H+2H; 9.15ppm 1H exchangeable; 11-11.4 ppm 1H exchangeable |

TABLE I-continued

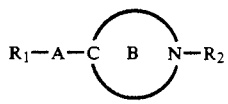

| EX-AMPLE No. | R₁ | A | B | R₂ | NMR SPECTRUM (Solvent) s = salt b = base |
|---|---|---|---|---|---|
| 7 | quinolin-3-yl | — | 1,2,3,6-tetrahydropyridin-4-yl | —CH₃ | $^1$H NMR (DMSO-d$_6$) s 3.0ppm m+s 5H; 3.4–3.75ppm m 2H; 4.0–4.2 ppm m 2H; 6.8ppm m 1H; 7.9ppm m 1H; 8.05 ppm m 1H; 8.25ppm d 1H 8.3ppm m 1H; 9.1 ppm d 1H; 9.5ppm d 1H; 5.5–7 1H exchangeable; 9.5–10.5ppm 1H exchangeable |
| 8 | quinolin-3-yl | — | 1,2,3,6-tetrahydropyridin-4-yl | —H | $^1$H NMR (DMSO-d$_6$) s 2.9ppm m 2H; 3.4–3.75 ppm m 2H; 4.0–4.2ppm m 2H; 6.8ppm m 1H; 7.9 ppm m 1H; 8.05ppm m 1H; 8.25ppm d 1H; 8.3 ppm m 1H; 9.1ppm d 1H; 9.5ppm d 1H; 5.5–7 1H exchangeable; 9.5–10.5ppm 1H exchangeable |
| 9 | quinolin-3-yl | — | piperidin-4-yl | —CH₃ | $^1$H NMR (DMSO-d$_6$) s 2.10ppm m 2H; 2.25ppm m 2H; 2.85ppm s 3H; 3.20ppm m 2H; 3.30ppm m 1H; 3.60ppm m 2H; 7.95ppm m 1H; 8.10ppm m 1H; 8.25ppm d 1H; 8.35ppm d 1H; 9.00ppm d 1H; 9.30ppm d 1H; 1.7–4ppm 1H exchangeable; 9–10.2ppm 1H exchangeable |
| 10 | quinolin-3-yl | — | piperidin-4-yl | —H | $^1$H NMR (DMSO-d$_6$) s 2.05ppm m 2H; 2.25ppm m 2H; 3.15ppm m 2H; 3.35ppm m 1H; 3.50ppm m 2H; 7.95ppm m 1H; 8.10ppm m 1H; 8.25ppm d 1H; 8.35ppm d 1H; 9.15ppm d 1H; 9.30ppm d 1H; 5.5–9ppm 2H exchangeable |
| 11 | quinolin-3-yl | — | piperidin-4-yl | —CH₂CN | $^1$H NMR (D$_2$O) s 2.1–2.4ppm m 2H; 2.45ppm m 2H; 3.35–3.6ppm m 1H; 3.45ppm m 2H; 3.85 ppm m 2H; 4.55ppm s 2H; 7.85–8.3ppm d+d+t+t 1H+1H+1H+1H; 9.10 ppm d 1H; 9.15ppm d 1H |
| 12 | quinolin-3-yl | — | piperidin-4-yl | —(CH₂)₂—NH—C(O)—C₆H₄—F | $^1$H NMR (DMSO-d$_6$) s 2.1–2.4ppm m 4H; 3.05–3.50 ppm m 5H; 3.6–3.9ppm m 4H; 7.3ppm t 2H; 7.90 ppm td 1H; 7.95–8.15 ppm m 3H; 8.3ppm m 2H; 8.85ppm d 1H; 9.1 ppm 1H exchangeable; 9.2ppm d 1H; 10.7–11.0 ppm 1H exchangeable |

TABLE I-continued

R₁—A—C⟨B⟩N—R₂

| EX-AMPLE No. | R₁ | A | B | R₂ | NMR SPECTRUM (Solvent) s = salt b = base |
|---|---|---|---|---|---|
| 13 | 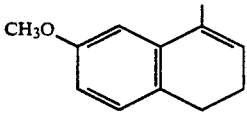 | —CH₂— | 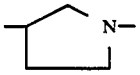 | —CH₂— 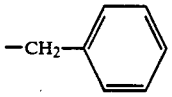 | ¹H NMR (CDCl₃) b 1.55 ppm m 1H; 2.0ppm m 2H; 2.25ppm m 2H; 2.6-2.3ppm m 5H; 2.7 ppm t 2H; 2.8ppm m 1H; 3.7-3.5ppm 2d 2H; 3.8 ppm s 3H; 5.85ppm t 1H; 6.6ppm dd 1H; 6.8ppm d 1H; 7.05ppm d 1H; 7.4-7.2m 5H |
| 14 | 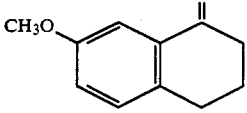 | =CH— | 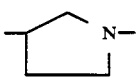 | —CH₂— 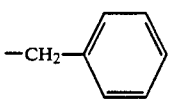 | ¹H NMR (CDCl₃) b 1.55ppm m 1H; 1.8ppm m 1H; 2ppm m 1H; 2.6-2.3ppm m+t+m 2H+2H+2H; 2.9ppm t 2H; 3.2ppm m 1H; 3.7-3.5ppm 2d 2H; 3.8ppm s 3H; 5.95ppm dd 1H; 6.75 ppm dd 1H; 6.95ppm d 1H; 7.15ppm d 1H; 7.4-7.2ppm m 5H |
| 15 | 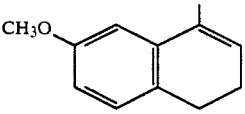 | — |  | —CH₃ | ¹H NMR (CDCl₃) b 1.6 ppm m 2H; 1.85ppm m 2H; 2.1-2.2ppm m 4H; 2.3ppm s 3H; 2.45ppm m 1H; 2.65ppm m 2H; 3.00 ppm m 2H; 3.8ppm s 3H; 5.9ppm m 1H; 6.7ppm dd 1H; 6.8ppm d 1H; 7.1 ppm d 1H |
| 16 | 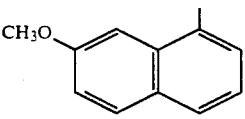 | — | 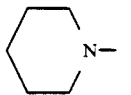 | —CH₃ | ¹H NMR (CDCl₃) b 1.8-2.1ppm m 4H; 2.2 ppm m 2H; 2.4ppm s 3H; 3-3.3ppm m 3H; 3.95ppm s 3H; 7.15ppm dd 1H; 7.2-7.45ppm m 3H; 7.9 ppm d 1H; 7.8ppm d 1H |
| 17 | 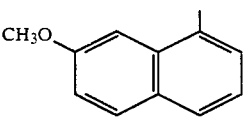 | — | 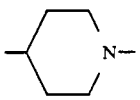 | —H | ¹H NMR (DMSO-d₆) s 1.8-2.1ppm m 4H; 3.1-3.5ppm m 4H; 3.5-3.8 ppm m 1H; 3.9ppm s 3H; 7.2ppm dd 1H; 7.3 ppm m 2H; 7.45ppm d 1H; 7.75ppm m 1H; 7.85 ppm d 1H; 9-9.5ppm 2H exchangeable |
| 18 | 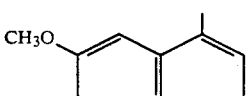 | — | 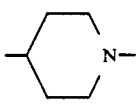 | —(CH₂)₂—NH—C(=O)—⟨C₆H₄⟩—F | ¹H NMR (DMSO-d₆) s 1.9-2.4ppm m 4H; 3.1-3.9ppm m 9H; 3.9ppm s 3H; 7.1-7.4ppm m+t+d+dd 2H+1H+1H+1H; 7.45 ppm d 1H; 7.7ppm m 1H; 7.85ppm d 1H; 8.05 ppm dd 2H; 9-10.7ppm 2H exchangeable |
| 19 | 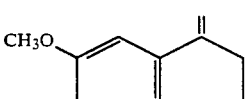 | = | 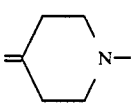 | —H | ¹H NMR (DMSO-d₆) s 1.7ppm m 2H; 2.3-2.6 ppm t+t 2H+2H; 2.6 ppm t 2H; 2.75ppm t 2H; 3.1ppm m 2H; 3.4ppm m 2H; 3.75ppm s 3H; 6.65 ppm d 1H; 6.7ppm dd 1H; 7.05ppm d 1H; 9.3 ppm 1H exchangeable |

TABLE I-continued

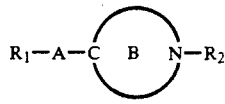

| EX-AMPLE No. | R₁ | A | B | R₂ | NMR SPECTRUM (Solvent) s = salt b = base |
|---|---|---|---|---|---|
| 20 | 7-methoxy-3,4-dihydronaphthalen-1(2H)-ylidene (CH₃O-) | = | piperidin-4-ylidene | —CH₂CN | $^1H$ NMR (CDCl₃) b 1.85ppm q 2H; 2.5ppm t 2H; 2.5-2.7ppm m 8H; 2.75ppm t 2H; 3.55ppm d 2H; 3.8ppm s 3H; 6.7m 2H; 7.05ppm d 1H |
| 21 | 7-methoxy-3,4-dihydronaphthalen-1(2H)-ylidene (CH₃O-) | = | piperidin-4-ylidene | —(CH₂)₂—NH—C(=O)—C₆H₄—F | $^1H$ NMR (CDCl₃) b 1.2 ppm q 2H; 2.3-2.8 ppm m 14H; 3.55ppm q 2H; 3.8ppm s 3H; 6.75 ppm m 2H; 7.0-7.3ppm m 3H; 7.85ppm dd 2H |
| 22 | 2,3-dihydro-1,4-benzodioxin-5-yl | — | 1,2,3,6-tetrahydropyridin-4-yl | —CH₂—C₆H₅ | $^1H$ NMR (CDCl₃) b 2.8-2.4ppm m 4H; 3.1 ppm m 2H; 3.6ppm s 2H; 4.2ppm s 4H; 5.8ppm m 1H; 6.75ppm m 3H; 7.3 ppm m 5H |
| 23 | 2,3-dihydro-1,4-benzodioxin-5-yl | — | 1,2,3,6-tetrahydropyridin-4-yl | —(CH₂)₂—NH—C(=O)—C₆H₄—F | $^1H$ NMR (CDCl₃) b 2.7-3.8ppm m 6H; 3.8-4.25ppm m 4H; 4.25ppm m 4H; 5.8ppm m 1H; 6.65-6.9ppm m 3H; 7.15 ppm t 2H; 8.2ppm dd 2H; 9 and 12.2 ppm 2H exchangeable |

PHARMACOLOGICAL STUDY

EXAMPLE 34

Evaluation of the Antihypertensive activity of the Compounds of the Invention

Mongrel dogs (males and females) were anesthetized with phenobarbital (30 mg/kg i.v.) and then placed under artificial respiration (Bird Mark VII respirator). The arterial pressure was measured using a catheter placed in the abdominal aorta via the femoral artery. This catheter is connected to a pressure cell (Statham ® R₂₃D₆) connected to a recorder.

The heart rate was measured using a Gould Biotach ®.

The sympathetic nervous activity was recorded at the level of the renal nerve using a silver electrode. The amplified signal was displayed on an oscilloscope (Tektronix 5115 ®) and then measured in UV using a Gould integrator. The compounds to be examined were administered intravenously.

The results of this study, indicated in Table II, have demonstrated that the compounds of the invention are more active than, or at least comparable with, the reference product flesinoaxan, in racemic form or in the form of an isomer (+). This isomer is the most active isomer of flesinoxan.

TABLE II

| COMPOUNDS | EFFECT ON THE ARTERIAL PRESSURE (mmHg) | EFFECT ON THE CARDIAC RHYTHM (B/min) | DOSES μg/kg |
|---|---|---|---|
| Flesinoxan (+) Isomer | ↘ #10 ↘ 10-30 ↘ >30 | ↘ #15 ↘ 15-30 ↘ >40 | 10 30 100 |

TABLE II-continued

| COMPOUNDS | EFFECT ON THE ARTERIAL PRESSURE (mmHg) | EFFECT ON THE CARDIAC RHYTHM (B/min) | DOSES µg/kg |
|---|---|---|---|
| Flesinoxan racemic | 0 | 0 | 10 |
|  |  | 0 | 30 |
|  | ↘ #10 |  | 100 |
|  |  | ↘ #15 | 300 |
|  | ↘ 10–30 |  |  |
|  |  | ↘ 15–35 |  |
|  | ↘ >30 |  |  |
| Compounds of the invention |  |  | 3–10 |
|  |  |  | 10–30 |
|  | ↘ #10 | ↘ #15 | 30–100 |
|  | ↘ 10–30 | ↘ 15–30 |  |
|  | ↘ >30 | ↘ 30–40 |  |

With regard to the sympathetic nervous activity, the results obtained with the compound of Example 18 after i.v. administration of a dose of 30 µg/kg are given in FIG. 1.

EXAMPLE 35

Evaluation of the Affinity for 5-HT$_{1A}$ Receptors

Hippocampus tissue obtained from decapitated Wistar rats was used for the studies. The animals were sacrificed 48 hours before the experiment and the isolated tissues were stored at −86° C. For preparation of the membranes, the tissues were then homogenized using 20 volumes of a 50 mM Tris HCl buffer solution (pH =7.7, adjusted using NH$_4$Cl at 25° C.) for one volume of tissue, at a temperature close to 0° C., using a Polytron ® homogenizer, and the whole was then centrifuged. (35,000 g×20 min at 4° C.). The pellet thus obtained was suspended in 100 volumes of an incubation buffer solution. (60 mM Tris, 10 µM pargyline, 4 mM CaCl$_2$ and 0.1% (wt/v) ascorbic acid; pH adjusted to 7.7 with 5N HCl). The compounds to be examined were also diluted in the incubation buffer and the solutions were then prepared by adding 100 µl of a solution of the compound to be examined and 100 µl of a solution of [3H] 8-OH-DPAT C =0.4 nM (specific radioactivity =205 Ci/mmol) to 12×75 mm glass tubes. The nonspecific binding was determined using a 10 µM 5-hydroxytryptamine solution and corresponds to 5–10% of the total binding.

The tubes were incubated for 30 min at 37° C. and the solutions were then filtered through GF/B glass fiber filters treated with 0.1% of polyethyleneimine (Whatman ®). The filters were rinsed twice with 5 ml of the incubation buffer solution and were then placed in ampoules to which 4.5 ml of "Picofluor scintillation fluid" ® (Packard) had been added. The radioactivity was determined using external standards.

The pKi were evaluated using the Cheung-Prusoff equation:

$$-\log (IC_{50}/[1+[3H]8\text{-}OH\text{-}DPAT]/Kd).$$

The compounds of the invention have a high affinity for the 5-HT$_{1A}$ sites. The pKi of the compounds of the invention are of the order of 9.02 moles/liter.

| PHARMACEUTICAL PREPARATION EXAMPLE 36 ||
|---|---|
| Capsules containing 1 mg of 1-[2-(4-fluorobenzamido)eth-1-yl]-4-(7-methoxynaphth-1-yl)piperidine hydrochloride [F.A.E.M.N.P] ||
| F.A.E.M.N.P. | 1 mg |
| Corn starch | 15 mg |
| Lactose | 25 mg |
| Talc | 5 mg |

We claim:

1. A compound selected from those of the formula I:

$$R_1-A-\boxed{C\ B\ N}-R_2 \quad (I)$$

in which

R$_1$ represents a naphthyl radical, of formula y$_1$:

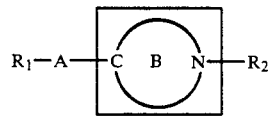

(y$_1$)

a dihydronaphthyl radical, of formula y$_2$:

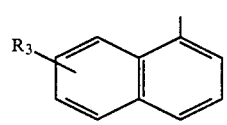

(y$_2$)

a tetrahydronaphthyl radical of formula y$_3$:

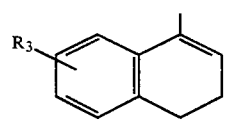

(y$_3$)

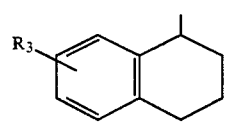

(in which formulae R$_3$ represents hydrogen, halogen, alkyl having 1 to 6 carbon atoms inclusive hydroxyl, or an alkoxy having 1 to 6 carbon atoms inclusive), A represents a single bond, a double bond (on condition, however, that $R_1$ represents a tetrahydronaphthyl radical), $R_2$ represents:

an aminoalkyl having 1 to 6 carbon atoms inclusive, cyanoalkyl having 1 to 6 carbon atoms inclusive or a radical of formula $w_1$:

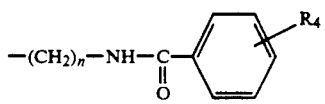

in which:

n is 1–6 inclusive and $R_4$ represents hydrogen, halogen, alkyl having 1 to 6 carbon atoms inclusive or alkoxy having 1 to 6 carbon atoms, its possible stereoisomers, and its addition salts with a pharmaceutically-acceptable acid.

2. The compound as claimed in claim 1 which is selected from 1-[2-(4-fluorobenzamido)eth-1-yl]-1-yl]-4-(7-methoxynaphth-1-yl) piperidine, and its addition salts with a pharmaceutically-acceptable acid.

3. A method for treating a living animal or human afflicted with a hypertensive condition requiring an agonist for 5-HT$_{1A}$ receptors comprising the step of administering to the said living animal or human an amount of a compound of claim 1 which is effective for alleviation of said condition.

4. A method as claimed in claim 3 for treating an animal or human afflicted with hypertension.

5. A pharmaceutical composition useful for treating a condition requiring a 5-HT$_{1A}$ agonist comprising as active principle an effective 5-HT$_{1A}$ receptor agonistic amount of a compound as claimed in claim 1, in combination with a pharmaceutically-acceptable excipient or vehicle.

6. The compound as claimed in claim 1 which is selected from 1-[2-(4-fluorobenamido)eth-1-yl]-4-(7-methoxynaphth-1-yl) piperidine hydrochloride.

* * * * *

UNITED STATES PATENT AND TRADEMARK OFFICE
CERTIFICATE OF CORRECTION

PATENT NO. : 5,250,544
DATED : October 5, 1993
INVENTOR(S) : Gilbert Lavielle, Michel Laubie, Francis Colpaert It is certified that error appears in the above-indentified patent and that said Letters Patent is hereby corrected as shown below:

TITLE PAGE, item [54] the title, line 1; insert a comma after the word "PIPERIDINE"

TITLE PAGE, item [57] ABSTRACT 4th line from the end; insert a comma after the word "atoms"

TITLE PAGE, item [57] ABSTRACT 3rd line from the end; delete the comma at the beginning of the line.

Column 1, line 1; insert a comma after the word "PIPERIDINE"

Column 11, line 16; "2H" should read -- 2H; --

Column 12, line 7; "pp" should read -- ppm --
Column 13, line 23; "100 3" should read -- 100:3 --
Column 15, line 23; "1M 1.5M" should read -- 1M:1.5M --

Column 29, line 45; "the solutions" should read -- the test solutions --
Column 31, line 1; delete the word "an"
Column 31, line 7; delete the word "an"

UNITED STATES PATENT AND TRADEMARK OFFICE
CERTIFICATE OF CORRECTION

PATENT NO. : 5,250,544
DATED : October 5, 1993
INVENTOR(S) : Gilbert Lavielle, Michel Laubie, Francis Colpaert It is certified that error appears in the above-indentified patent and that said Letters Patent is hereby corrected as shown below:

Column 31, line 23; insert the word -- inclusive -- after the word "atoms" and before the comma.(Prel.Amdt.7-1-91)
Column 32, line 4; delete "-1-yl]" second occurrence Column 32, line 22; "(4-fluorobenamido)" should read -- (4-fluorobenzamido) --

Signed and Sealed this

Seventeenth Day of January, 1995

Attest:

BRUCE LEHMAN

Attesting Officer  Commissioner of Patents and Trademarks

UNITED STATES PATENT AND TRADEMARK OFFICE
CERTIFICATE OF CORRECTION

PATENT NO. : 5,250,544

DATED : October 5, 1993

INVENTOR(S) : Gilbert Lavielle, Michel Laubie and Francis Colpaert

It is certified that error appears in the above-indentified patent and that said Letters Patent is hereby corrected as shown below:

Column 16, line 34; "520" should read -- 520 g --

Signed and Sealed this

Twenty-third Day of May, 1995

Attest:

BRUCE LEHMAN

*Attesting Officer*    *Commissioner of Patents and Trademarks*